United States Patent
Kerr

(10) Patent No.: US 8,226,650 B2
(45) Date of Patent: Jul. 24, 2012

(54) APPARATUS, SYSTEM, AND METHOD FOR PERFORMING AN ENDOSCOPIC ELECTROSURGICAL PROCEDURE

(75) Inventor: Duane E. Kerr, Loveland, CO (US)

(73) Assignee: TYCO Healthcare Group LP, Mansfield, MA (US)

( * ) Notice: Subject to any disclaimer, the term of this patent is extended or adjusted under 35 U.S.C. 154(b) by 604 days.

(21) Appl. No.: 12/411,542

(22) Filed: Mar. 26, 2009

(65) Prior Publication Data

US 2010/0249776 A1    Sep. 30, 2010

(51) Int. Cl.
*A61B 18/14* (2006.01)

(52) U.S. Cl. .......................................................... 606/51

(58) Field of Classification Search .................. 606/51, 606/31, 41, 33, 34
See application file for complete search history.

(56) References Cited

U.S. PATENT DOCUMENTS

| | | | |
|---|---|---|---|
| 4,655,216 A * | 4/1987 | Tischer | 606/51 |
| 5,209,747 A | 5/1993 | Knoepfler | |
| 5,211,655 A | 5/1993 | Hasson | |
| 5,403,312 A * | 4/1995 | Yates et al. | 606/50 |
| 5,558,671 A * | 9/1996 | Yates | 606/38 |
| 5,611,813 A | 3/1997 | Lichtman | |
| 5,620,459 A | 4/1997 | Lichtman | |
| 5,674,220 A * | 10/1997 | Fox et al. | 606/51 |
| 5,762,609 A * | 6/1998 | Benaron et al. | 600/473 |
| 5,935,126 A | 8/1999 | Riza | |
| 6,152,923 A * | 11/2000 | Ryan | 606/51 |
| 6,171,316 B1 | 1/2001 | Kovac et al. | |
| 6,569,105 B1 | 5/2003 | Kortenbach et al. | |
| 6,623,482 B2 * | 9/2003 | Pendekanti et al. | 606/51 |
| 6,656,177 B2 * | 12/2003 | Truckai et al. | 606/51 |
| 6,663,641 B1 | 12/2003 | Kovac et al. | |
| 6,682,528 B2 * | 1/2004 | Frazier et al. | 606/51 |
| 6,743,240 B2 | 6/2004 | Smith et al. | |
| 6,770,072 B1 | 8/2004 | Truckai et al. | |
| 6,821,285 B2 | 11/2004 | Laufer et al. | |
| 7,101,371 B2 * | 9/2006 | Dycus et al. | 606/49 |
| 7,150,097 B2 * | 12/2006 | Sremcich et al. | 29/854 |
| 2002/0115997 A1 * | 8/2002 | Truckai et al. | 606/51 |

(Continued)

FOREIGN PATENT DOCUMENTS

CA    2104423    2/1994

(Continued)

OTHER PUBLICATIONS

U.S. Appl. No. 12/336,970, filed Dec. 17, 2008.

(Continued)

*Primary Examiner* — Kevin C Sirmons
*Assistant Examiner* — Michael J Anderson

(57) ABSTRACT

A bipolar forceps includes an end effector assembly having a flexible jaw member and a fixed jaw member. The flexible jaw member has a flange operably coupled to the fixed jaw member about a pivot. A drive assembly is configured to pivot the flexible jaw member relative to the fixed jaw member from a first position and a second position. A handle is movable between an open position when the jaw members are disposed in the first position and a closed position to cause the drive assembly to rotate the flange about the pivot in a second direction to move the jaw members to the second position. A distal end of the flexible jaw member is configured to engage the fixed jaw member prior to a proximal portion of the flexible jaw member upon movement of the jaw members to the second position.

17 Claims, 5 Drawing Sheets

U.S. PATENT DOCUMENTS

| | | | |
|---|---|---|---|
| 2003/0018331 A1* | 1/2003 | Dycus et al. ............... | 606/48 |
| 2003/0114851 A1* | 6/2003 | Truckai et al. ............. | 606/51 |
| 2003/0220637 A1* | 11/2003 | Truckai et al. ............. | 606/28 |
| 2005/0203504 A1* | 9/2005 | Wham et al. ............... | 606/34 |
| 2006/0064085 A1* | 3/2006 | Schechter et al. ........ | 606/50 |
| 2007/0173814 A1 | 7/2007 | Hixson et al. | |
| 2008/0319442 A1 | 12/2008 | Unger et al. | |
| 2009/0012520 A1 | 1/2009 | Hixson et al. | |
| 2009/0182327 A1 | 7/2009 | Unger | |

FOREIGN PATENT DOCUMENTS

| | | |
|---|---|---|
| DE | 2415263 | 10/1975 |
| DE | 2514501 | 10/1976 |
| DE | 2627679 | 1/1977 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 29616210 | 1/1997 |
| DE | 19608716 | 4/1997 |
| DE | 19751106 | 5/1998 |
| DE | 19751108 | 5/1999 |
| DE | 19738457 | 1/2009 |
| EP | 1159926 | 12/2001 |
| EP | 1177771 A1 | 2/2002 |
| GB | 623316 | 5/1949 |
| GB | 1490585 | 11/1977 |
| GB | 2214430 A | 6/1989 |
| GB | 2213416 A | 8/1989 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO94/02005 | 9/1994 |

OTHER PUBLICATIONS

U.S. Appl. No. 12/339,614, filed Mar. 6, 2009.
U.S. Appl. No. 12/195,624, filed Aug. 21, 2008.
U.S. Appl. No. 12/367,791, filed Feb. 9, 2009.
U.S. Appl. No. 12/361,367, filed Jan. 28, 2009.
U.S. Appl. No. 12/361,375, filed Jan. 28, 2009.
U.S. Appl. No. 12/400,901, filed Mar. 10, 2009.
U.S. Appl. No. 12/176,679, filed Jul. 21, 2008.
U.S. Appl. No. 12/237,515, filed Sep. 25, 2008.
U.S. Appl. No. 12/204,976, filed Sep. 5, 2008.
U.S. Appl. No. 12/192,170, filed Aug. 15, 2008.
U.S. Appl. No. 12/333,157, filed Sep. 18, 2008.
U.S. Appl. No. 12/237,582, filed Sep. 25, 2008.
U.S. Appl. No. 12/210,598, filed Sep. 15, 2008.
U.S. Appl. No. 12/200,154, filed Aug. 28, 2008.
U.S. Appl. No. 12/211,205, filed Sep. 16, 2008.
U.S. Appl. No. 12/244,873, filed Oct. 3, 2008.
U.S. Appl. No. 12/246,553, filed Oct. 7, 2008.
U.S. Appl. No. 12/248,115, filed Oct. 9, 2008.
U.S. Appl. No. 12/353,474, filed Jan. 14, 2009.
U.S. Appl. No. 12/353,470, filed Jan. 14, 2009.
U.S. Appl. No. 12/352,942, filed Jan. 13, 2009.
U.S. Appl. No. 12/237,556, filed Sep. 25, 2008.
U.S. Appl. No. 12/411,542, filed Mar. 26, 2009.
U.S. Appl. No. 12/248,104, filed Oct. 9, 2008.
U.S. Appl. No. 12/254,123, filed Oct. 20, 2008.
U.S. Appl. No. 12/200,246, filed Aug. 28, 2008.
U.S. Appl. No. 12/200,396, filed Aug. 28, 2008.
U.S. Appl. No. 12/200,526, filed Aug. 28, 2008.
U.S. Appl. No. 12/236,666, filed Sep. 24, 2008.
U.S. Appl. No. 12/192,189, filed Aug. 15, 2008.
U.S. Appl. No. 12/192,243, filed Aug. 15, 2008.
U.S. Appl. No. 12/331,643, filed Dec. 10, 2008.
U.S. Appl. No. 12/353,466, filed Jan. 14, 2009.
U.S. Appl. No. 12/363,086, filed Jan. 30, 2009.
U.S. Appl. No. 12/419,729, filed Apr. 7, 2009.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Carus et al., "Initial Experience With The LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.

"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2 dated Jun. 15, 2009.
Int'l Search Report EP 09 152898.4 dated Jun. 10, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.

* cited by examiner

APPARATUS, SYSTEM, AND METHOD FOR PERFORMING AN ENDOSCOPIC ELECTROSURGICAL PROCEDURE

BACKGROUND

1. Technical Field

The present disclosure relates to an apparatus, system, and method for performing an endoscopic electrosurgical procedure. More particularly, the present disclosure relates to an apparatus, system, and method for performing an endoscopic electrosurgical procedure that employs an endoscopic electrosurgical apparatus that includes an end effector assembly configured for use with various size access ports.

2. Description of Related Art

Electrosurgical apparatuses (e.g., electrosurgical forceps) are well known in the medical arts and typically include a handle, a shaft and an end effector assembly operatively coupled to a distal end of the shaft that is configured to manipulate tissue (e.g., grasp and seal tissue). Electrosurgical forceps utilize both mechanical clamping action and electrical energy to effect hemostasis by heating the tissue and blood vessels to coagulate, cauterize, seal, cut, desiccate, and/or fulgurate tissue As an alternative to open electrosurgical forceps for use with open surgical procedures, many modern surgeons use endoscopes and endoscopic electrosurgical apparatus (e.g., endoscopic forceps, laparoscopic forceps) for remotely accessing organs through smaller, puncture-like incisions. As a direct result thereof patients tend to benefit from less scarring and reduced healing time. Typically, the endoscopic forceps are inserted into the patient through one or more various types of cannulas or access ports (typically having an opening that ranges from about five millimeters to about twelve millimeters) that has been made with a trocar; as can be appreciated, smaller cannulas are usually preferred.

Endoscopic forceps that are configured for use with small cannulas (e.g., cannulas less than five millimeters) may present design challenges for a manufacturer of endoscopic instruments.

SUMMARY

According to an embodiment of the present disclosure, a bipolar forceps includes an end effector assembly having a flexible jaw member and a fixed jaw member. The flexible jaw member has a flange extending therefrom operably coupled to the fixed jaw member about a pivot. A drive assembly is operably coupled to the flange and is configured to pivot the flexible jaw member relative to the fixed jaw member from a first position wherein the flexible jaw member is disposed in spaced relation relative to the fixed jaw member and a second position wherein the flexible jaw member is closer to the fixed jaw member. A handle is operably coupled to the drive assembly and is movable between an open position when the jaw members are disposed in the first position and a closed position to cause the drive assembly to rotate the flange about the pivot in a second direction to move the jaw members to the second position. A distal end of the flexible jaw member is configured to engage the fixed jaw member prior to a proximal portion of the flexible jaw member upon movement of the jaw members to the second position such that the proximal portion is configured to flex toward the fixed jaw member when the distal end of the flexible jaw member contacts the fixed jaw member to grasp tissue between the jaw members.

According to another embodiment of the present disclosure, a bipolar forceps includes a housing having a shaft that extends from the housing. The shaft defines a longitudinal axis and has an end effector assembly at its distal end. The end effector assembly has a movable flexible jaw member and an inflexible jaw member. The flexible jaw member has a flange operably coupled to the inflexible jaw member about a pivot. Each of the flexible jaw member and the inflexible jaw member are adapted to connect to a source of electrical energy such that electrical energy can be conducted through tissue to effect a seal. A drive assembly is operably coupled to the flange and is configured to rotate the flange about the pivot to move the flexible jaw member relative to the inflexible jaw member from a first position wherein the flexible jaw member is disposed in spaced relation relative to the inflexible jaw member and a second position wherein the flexible jaw member is closer to the inflexible jaw member. A handle is operably coupled to the drive assembly and is movable between an open position to cause distal movement of the drive assembly which rotates the flange in a first direction about the pivot to move the jaw members to the first position and a closed position to cause proximal movement of the drive assembly which rotates the flange in a second direction about the pivot to move the jaw members to the second position to maintain a predetermined closure force between the jaw members. The handle is configured, when in the closed position, to generate additional torque about the pivot to impart a load on the drive assembly to vary the predetermined closure force between the jaw members.

According to another embodiment of the present disclosure, a method of utilizing a bipolar forceps includes the step of providing an end effector assembly having a flexible jaw member operably coupled to a fixed jaw member about a pivot. The method also includes the step of pivoting the flexible jaw member relative to the fixed jaw member from a first position, wherein the flexible jaw member is disposed in spaced relation relative to the fixed jaw member, and a second position wherein a distal end of the flexible jaw member is configured to engage the fixed jaw member prior to a proximal portion thereof such that the proximal portion is configured to flex toward the fixed jaw member when the distal end of the flexible jaw member contacts the fixed jaw member to grasp tissue between the jaw members.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, the disclosed embodiments are merely exemplary of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

As noted above, it may prove useful in the arts to provide an electrosurgical apparatus that is suitable for use with various access ports, including but not limited to those that are greater than and/or less than five millimeters. With this purpose in mind, the present disclosure includes an electrosurgical forceps that includes a drive assembly operatively coupled to one or more jaw members associated with the end effector assembly of the electrosurgical forceps. One or both of the jaw members is tip-biased and configured to flex or bend closed. That is, after a distal end of a tip-biased jaw member engages tissue, the middle and/or rear portions of the tip-biased jaw member flexes or bends to engage tissue. The drive assembly is configured to move the jaws from an open to a closed configuration that forms a closed loop electrical circuit such that a desired tissue effect (e.g., tissue seal) may be achieved.

Figure 1:
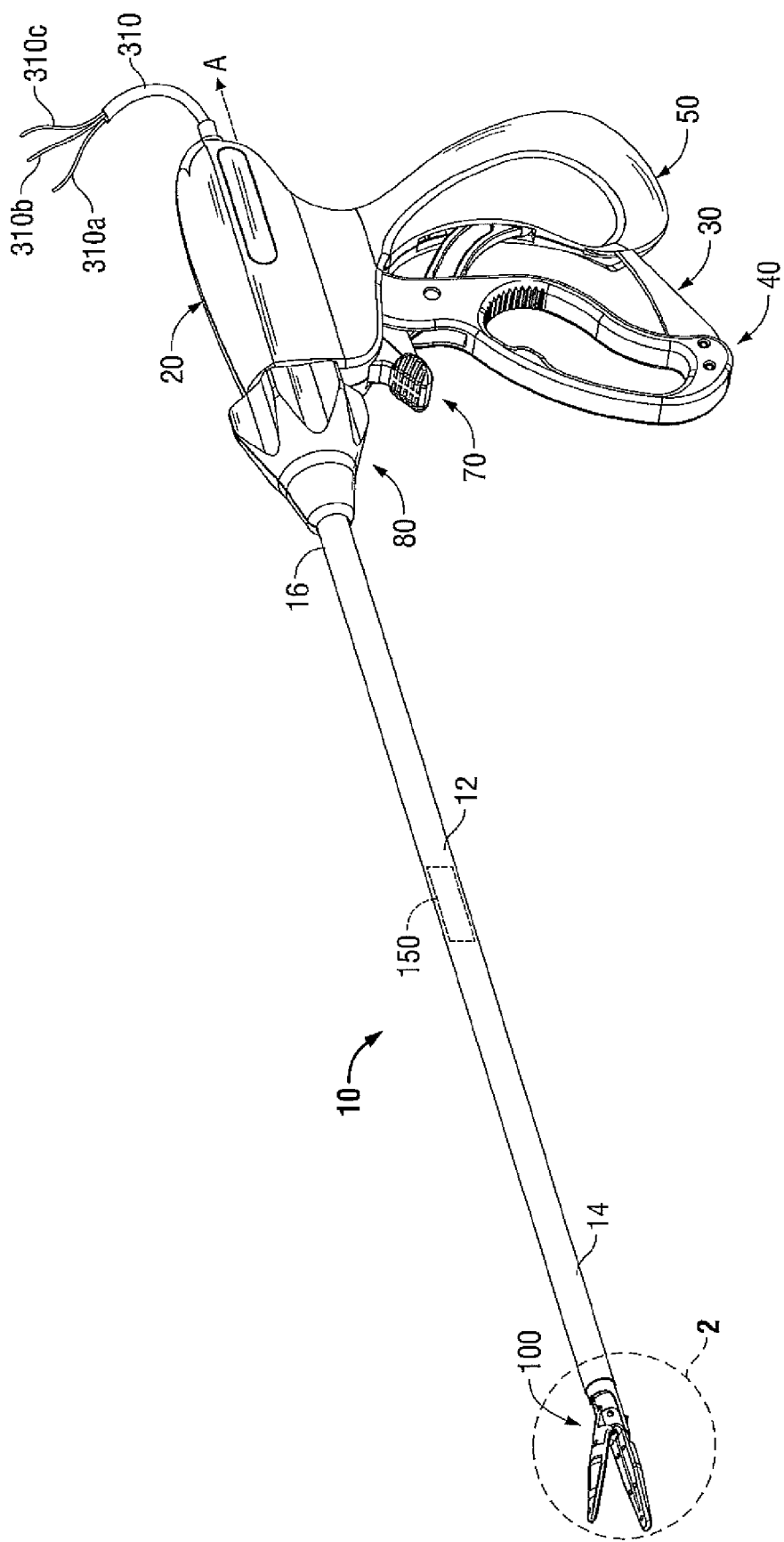
FIG. 1 is a right, perspective view of an endoscopic bipolar forceps showing a housing, a shaft, and an end effector assembly in accordance with the present disclosure.

Turning now to FIG. 1, an embodiment of an endoscopic bipolar forceps 10 is shown for use with various surgical procedures and generally includes a housing 20, a handle assembly 30, a rotating assembly 80, a trigger assembly 70, and an end effector assembly 100 that mutually cooperate to grasp, seal, and divide tubular vessels and vascular tissue. Although the majority of the figure drawings depict a bipolar forceps 10 for use in connection with endoscopic surgical procedures, the present disclosure may be used for more traditional open surgical procedures. For the purposes herein, the forceps 10 is described in terms of a laparoscopic instrument; however, it is contemplated that an open version of the forceps may also include the same or similar operating components and features as described below.

Forceps 10 includes a shaft 12 that has a distal end 14 dimensioned to mechanically engage the end effector assembly 100 and a proximal end 16 that mechanically engages the housing 20. In the drawings and in the descriptions that follow, the term "proximal", as is traditional, will refer to the end of the forceps 10 that is closer to the user, while the term "distal" will refer to the end that is further from the user.

Forceps 10 includes an electrosurgical cable 310 that connects the forceps 10 to a source of electrosurgical energy, e.g., a generator (not shown). One such source of electrosurgical energy is described in commonly-owned U.S. Pat. No. 6,033,399 entitled "ELECTROSURGICAL GENERATOR WITH ADAPTIVE POWER CONTROL". Cable 310 is internally divided into cable leads 310a, 310b, and 310c, that are designed to transmit electrical potentials through their respective feed paths through the forceps 10 to the end effector assembly 100.

For a more detailed description of handle assembly 30, movable handle 40, rotating assembly 80, and electrosurgical cable 310 (including line-feed configurations and/or connections) reference is made to commonly owned Patent Publication No., 2003-0229344, filed on Feb. 20, 2003, entitled VESSEL SEALER AND DIVIDER AND METHOD OF MANUFACTURING THE SAME.

Handle assembly 30 includes a fixed handle 50 and a movable handle 40. Fixed handle 50 is integrally associated with housing 20 and handle 40 is movable relative to fixed handle 50 as explained in more detail below with respect to the operation of the forceps 10. Rotating assembly 80 is operatively connected to the housing 20 and is rotatable approximately 180 degrees in either direction about a longitudinal axis "A-A" (See FIG. 1).

As mentioned above, end effector assembly 100 is attached at the distal end 14 of shaft 12 and includes a pair of opposing jaw members 110 and 120. Movable handle 40 of handle assembly 30 is operatively connected to a drive assembly 150 (shown in phantom) that, together, mechanically cooperate to impart movement of the jaw members 110 and 120 from an open position wherein the jaw members 110 and 120 are disposed in spaced relation relative to one another, to a clamping or closed position wherein the jaw members 110 and 120 cooperate to grasp tissue therebetween. With this purpose in mind, drive assembly 150 may include any suitable number of electrical connections, configurations, and/or components (e.g., resistors, capacitors, inductors, rheostats, etc.), mechanical connections, configurations, and/or components (e.g., gears, links, springs, rods, etc.), and/or electro-mechanical connections, configurations, and/or components such that forceps 10 may function as intended.

Figure 2:
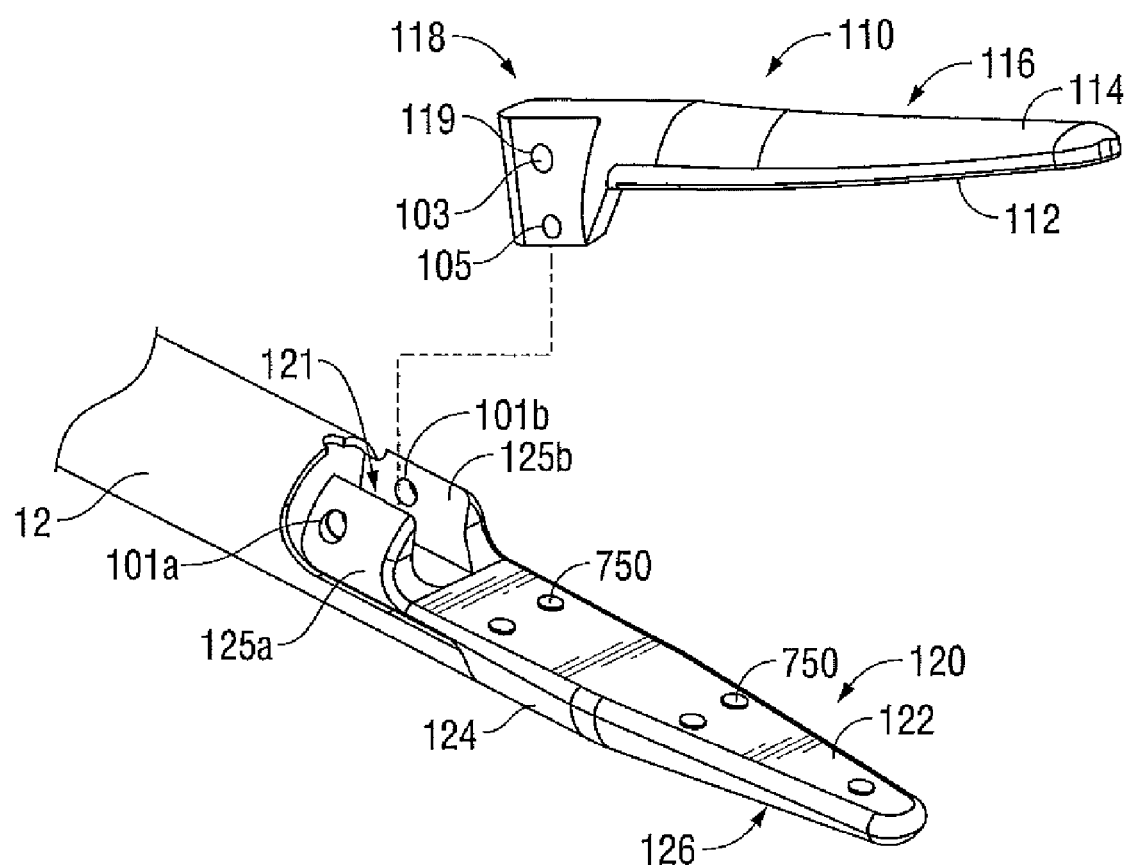
FIG. 2 is an enlarged, left perspective view of the end effector assembly of FIG. 1 with the jaw members shown in open configuration.
Figure 3A:
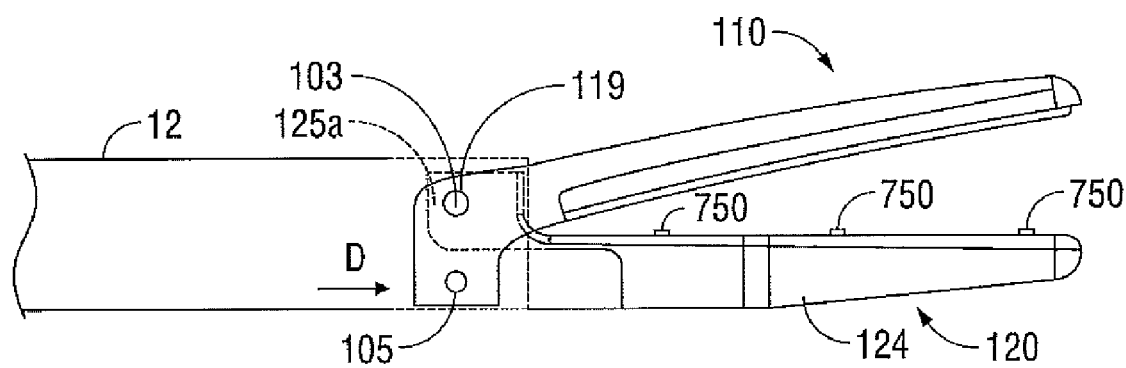
FIG. 3A is an enlarged, side view of the end effector assembly of FIG. 1 with the jaw members shown in open configuration.
Figure 3B:
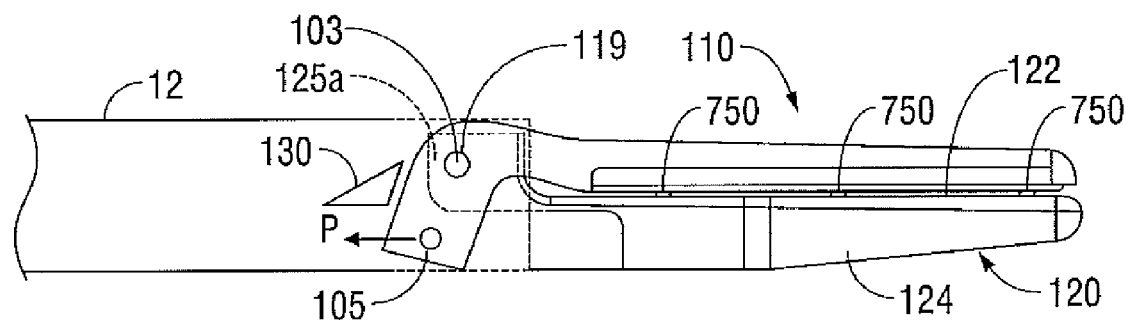
FIG. 3B is an enlarged, side view of the end effector assembly of FIG. 1 with the jaw members shown in closed configuration.

As shown best in FIGS. 2, 3A, and 3B, the end effector assembly 100 includes opposing jaw members 110 and 120 that cooperate to effectively grasp tissue for sealing purposes. The end effector assembly 100 may be designed as a unilateral assembly, i.e., jaw member 120 is fixed relative to the shaft 12 and jaw member 110 pivots about a pivot pin 103 relative to jaw member 120 to grasp tissue, or as a bilateral assembly, i.e., jaw members 110 and 120 pivot about pivot pin 103 relative to each other to grasp tissue. In some embodiments and as will be discussed in further detail below, jaw members 110, 120 are operably coupled to each other via pivot pin 103 about which pivoting jaw member 110 pivots relative to stationary jaw member 120.

In the illustrated embodiment, the unilateral end effector assembly 100 includes one stationary or fixed jaw member 120 mounted in fixed relation to the shaft 12 and a pivoting jaw member 110 mounted about a pivot pin 103 attached to the stationary jaw member 120. In some embodiments, fixed jaw member 120 may be monolithically formed with shaft 12, e.g., stationary jaw member 120 may be defined by the distal end 14 of shaft 12.

In some embodiments, pivoting jaw member 110 is formed from any suitable material having flexible properties, for example without limitation, metallic material such as aluminum and alloys thereof, plated brass, stainless steel, stainless steel alloys, beryllium copper, etc. The flexible nature of the jaw member 110 provides a jaw member 110 that is tip-biased and configured to flex closed. That is, a distal end of the jaw 110 is configured to engage and/or grasp tissue prior to a middle portion and/or a proximal or "rear" end of the jaw 110. More specifically, after the distal end of jaw member 110 engages tissue, the middle and/or proximal end of jaw member 110 are then caused to "flex" or "bend" inward toward the fixed jaw member 120 such that tissue may be grasped therebetween. The flexibility of jaw member 110 operates to allow precision generation of pressure on tissue grasped between jaw members 110 and 120 for purposes of sealing the tissue, as will be discussed in more detail below. In other embodiments, one or both of jaw members 110 and 120 may be formed from material having malleable or flexible properties or, alternatively, one or both of jaw members 110 and 120 may be formed from a material having inflexible properties.

Referring now to FIG. 2, jaw member 110 includes a pivot flange 118 having a mechanical interface 105 disposed thereon. Mechanical interface 105 may be, without limitation, a link, a gear, a pin, a rod, any combination thereof, or any interface suitable to operably couple pivot flange 118 to drive assembly 150, as will be discussed in further detail below. Pivot flange 118 also includes a pin slot 119 which is configured to engage pivot pin 103 to allow jaw member 110 to rotate relative to jaw member 120. More particularly, jaw member 120 includes a pair of proximal, upwardly extending flanges 125a and 125b which define a cavity 121 dimensioned to receive flange 118 of movable jaw member 110 therein. Each of the flanges 125a and 125b includes an aperture 101a and 101b, respectively, defined therethrough which secures pivot pin 103 on opposite sides of pivot mount 119 disposed within jaw member 110. As explained in further detail below, proximal movement of the drive assembly 150 engages mechanical interface 105 to pivot jaw member 110 to a closed position.

As best shown in FIGS. 3A and 3B, mechanical interface 105 is operable by the drive assembly 150 such that drive assembly 150 urges mechanical interface 105 in the distal and proximal directions, as indicated by directional arrows "D" and "P", respectively. The pivoting jaw member 110 is actuated by the drive assembly 150 such that the pivoting jaw member 110 pivots about pivot pin 103 between open and closed positions. Pulling the mechanical interface 105 proximally closes the jaw members 110 and 120 about tissue grasped therebetween and pushing the mechanical interface 105 distally opens the jaw members 110 and 120 for grasping purposes. In another embodiment illustrated in FIG. 3C, pivot pin 103 is configured to slide within a cam slot to pivot jaw member 110 between open and closed positions.

As best shown in FIG. 2, jaw member 110 also includes a jaw housing 116 which has an insulative substrate or insulator 114 and an electrically conducive surface 112. Insulator 114 is configured to securely engage the electrically conductive sealing surface 112. This may be accomplished by stamping, by overmolding, by overmolding a stamped electrically conductive sealing plate and/or by overmolding a metal injection molded seal plate.

All of these manufacturing techniques produce jaw member 110 having an electrically conductive surface 112 which is substantially surrounded by an insulating substrate 114. The insulator 114, electrically conductive sealing surface 112 and the outer, non-conductive jaw housing 116 are configured to limit and/or reduce many of the known undesirable effects related to tissue sealing, e.g., flashover, thermal spread and stray current dissipation. In other embodiments, the jaw members 110 and 120 may be manufactured from a ceramic-like material and the electrically conductive surface(s) 112 are coated onto the ceramic-like jaw members 110 and 120.

Jaw member 120 includes similar elements to jaw member 110 such as jaw housing 126 having an insulator 124 and an electrically conductive sealing surface 122 that is dimensioned to securely engage the insulator 124.

As best shown in FIG. 2, jaw member 120 may include a series of stop members 750 disposed on the inner facing surfaces of the electrically conductive sealing surface 122 to facilitate gripping and manipulation of tissue and to define a gap "G" (FIG. 4) between opposing jaw members 110 and 120 during scaling and cutting of tissue. As best shown in FIGS. 3A and 3B, pivoting jaw member 110 pivots about pivot pin 103 to the closed position such that conductive sealing surface 112 engages stop members 750. The flexible nature of jaw member 110 allows an operator to generate additional sealing pressure on tissue grasped between the jaw members 110 and 120. More specifically, once end effector assembly 100 is in the closed position and pivoting jaw member 110 is engaged with stop members 750 (FIG. 3B), movable handle 40 may be squeezed relative to stationary handle 50 to utilize the flexibility of jaw member 110 to vary and/or generate additional closure pressure between jaw member 110 and stop members 750 for purposes of sealing tissue. The series of stop members 750 may be employed on one or both jaw members 110 and 120 depending upon a particular purpose or to achieve a desired result. A detailed discussion of stop members 750 as well as various manufacturing and assembling processes for attaching and/or affixing the stop members 750 to the electrically conductive sealing surfaces 112, 122 are described in commonly owned, co-pending U.S. Patent Publication Application No. 20040122423 entitled "VESSEL SEALER AND DIVIDER WITH NON-CONDUCTIVE STOP MEMBERS" by Dycus et al.

Figure 3C:
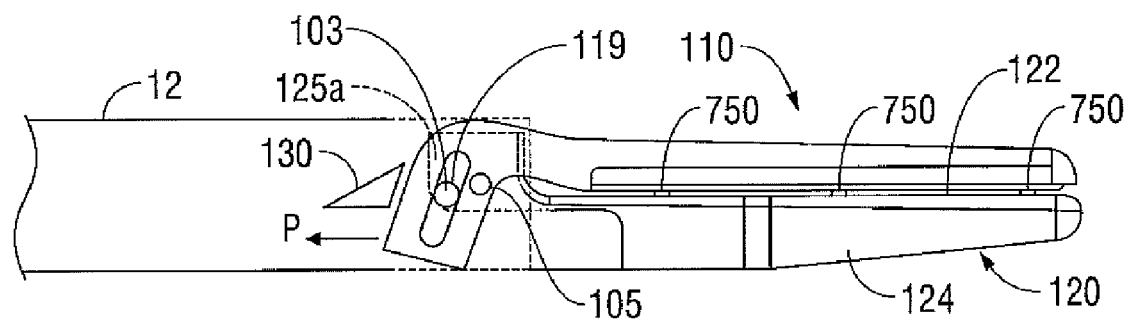
FIG. 3C is an enlarged, side view of an end effector assembly according to one embodiment of the present disclosure.

In some embodiments, as illustrated in FIGS. 3B and 3C, forceps 10 includes a camming member 130 disposed within shaft 12 and positioned to engage pivoting jaw member 110 at flange 118 when pivoting jaw member 110 is pivoted to the closed position. More specifically, as pivoting jaw member 110 pivots about pivot pin 103 from the open position to the closed position, i.e., in a clock-wise direction, camming member 130 cams a surface of flange 118 to prevent further pivoting of jaw member 110 about pivot pin 103 in the clock-wise direction. Once end effector assembly 100 is in the closed position, and camming member 130 is engaged with flange 118, movable handle 40 may be squeezed relative to stationary handle 50 to utilize the flexibility of jaw member 110 to vary and/or generate additional closure pressure between jaw members 110 and 120 and/or between jaw member 110 and stop members 750, as discussed hereinabove.

Figure 3D:
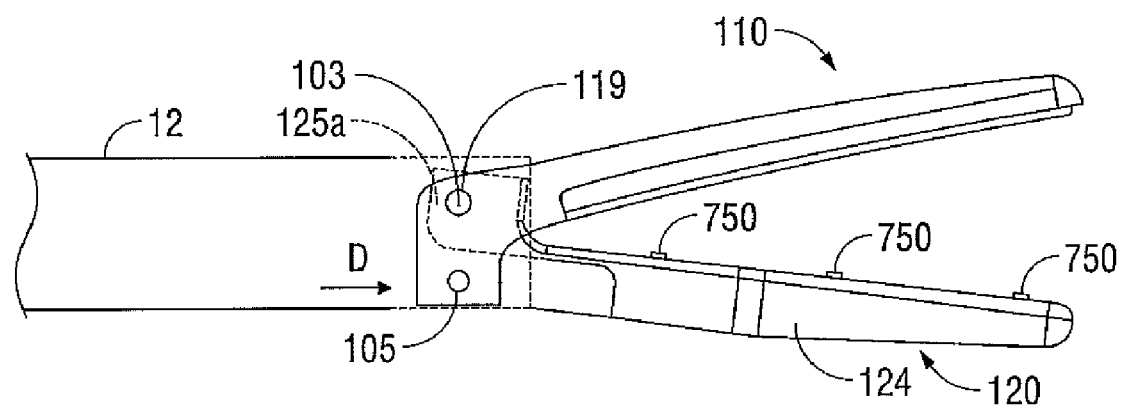
FIG. 3D is an enlarged, side view of an end effector assembly according to another embodiment of the present disclosure.

In some embodiments, as illustrated in FIG. 3D, the end effector assembly 100 may be designed as a bilateral assembly, i.e., each of jaw members 110 and 120 pivot about pivot pin 103 relative to each other to grasp tissue.

In the illustrated embodiment, the unilateral end effector assembly 100 includes one stationary or fixed jaw member 120 mounted in fixed relation to the shaft 12 and a pivoting jaw member 110 mounted about a pivot pin 103 attached to the stationary jaw member 120. In some embodiments, fixed jaw member 120 may be monolithically formed with shaft 12, e.g., stationary jaw member 120 may be defined by the distal end 14 of shaft 12.

Figure 4:
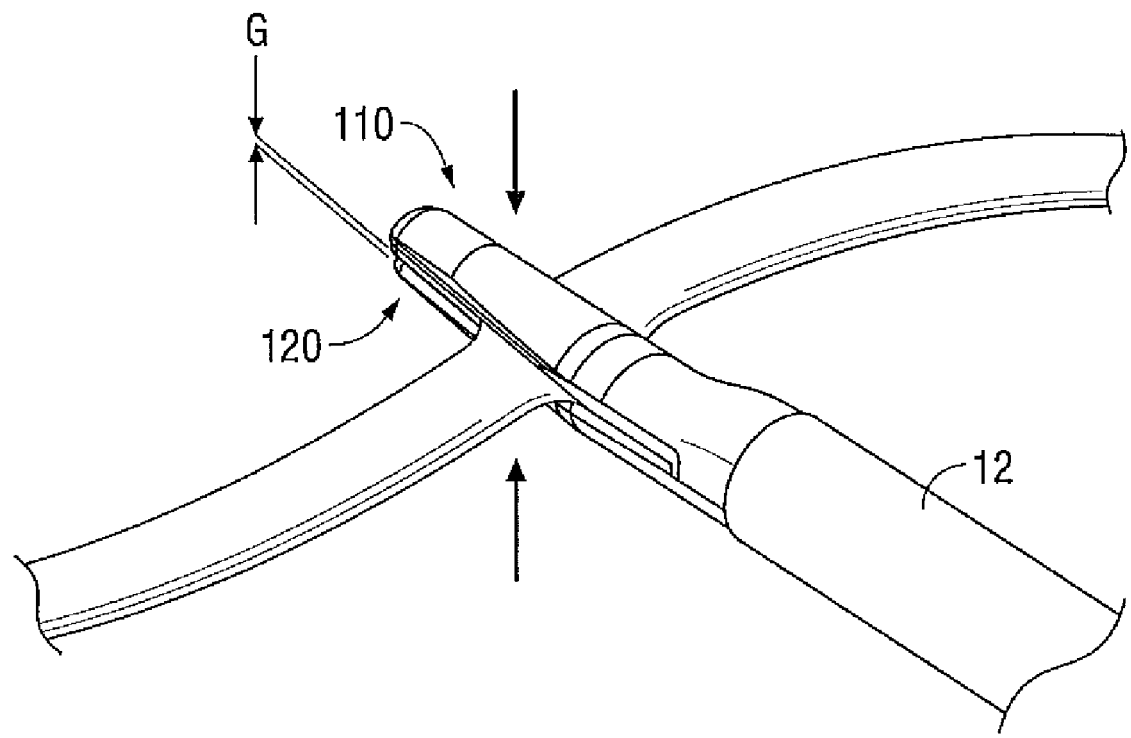
FIG. 4 is an enlarged, rear, perspective view of the end effectors shown grasping tissue.

FIG. 4 shows the forceps grasping tissue. As the handle 40 is squeezed, the mechanical interface 105 is pulled proximally by the movement of drive assembly 150 to rotate flange 118 clock-wise which, in turn, pivots jaw member 110 about pivot pin 103 to the closed position.

The mechanical advantage realized from the flexible nature of jaw member 110, as discussed hereinabove, will enable the operator to impart an additional load on the drive assembly 150 by squeezing handle 40 (e.g., through use of an operably coupled torsion spring). The drive assembly's 150 load is converted to a torque about the jaw pivot 103. As a result, a specific closure force can be transmitted to the opposing jaw members 110 and 120. Alternatively or additionally, stationary jaw member 120 may be formed from material having malleable or flexible properties to provide a mechanical advantage. Further, the jaw members 110 and 120 may be opened, closed and rotated to manipulate tissue until sealing is desired. This enables the user to position and re-position the forceps 10 prior to activation and sealing.

Once jaws members 110 and 120 are fully compressed about the tissue, the forceps 10 are now ready for selective application of electrosurgical energy and subsequent separation of the tissue.

The mechanical advantage provided by the flexible nature of one or both of jaw members 110 and 120 facilitates and assures consistent, uniform and accurate closure pressure about tissue within the desired working pressure range of about 3 kg/cm$^2$ to about 16 kg/cm$^2$ in one embodiment and, in another embodiment about 7 kg/cm$^2$ to about 13 kg/cm$^2$. By controlling the intensity, frequency and duration of the electrosurgical energy applied to tissue, the operator can either cauterize, coagulate/desiccate, seal and/or simply reduce or slow bleeding. Two mechanical factors play an important role in determining the resulting thickness of the sealed tissue and effectiveness of the seal, i.e., the pressure applied between opposing jaw members 110 and 120 and the gap distance "G" between the opposing sealing surfaces 112, 122 of the jaw members 110 and 120 during the sealing process.

As mentioned above, at least one jaw member, e.g., 120, may include a stop member 750 which limits the movement of the two opposing jaw members 110 and 120 relative to one another. The stop member 750 extends from the sealing surface 122 a predetermined distance according to the specific material properties (e.g., compressive strength, thermal expansion, etc.) to yield a consistent and accurate gap distance "G" during sealing (FIG. 4). In embodiments, the gap distance between opposing sealing surfaces 112 and 122 during sealing ranges from about 0.001 inches to about 0.006 inches and, in other embodiments, between about 0.002 and about 0.003 inches. The non-conductive stop members 750 may be, without limitation, molded onto the jaw members 110 and 120 (e.g., overmolding, injection molding, etc.), stamped onto the jaw members 110 and 120 or deposited (e.g., deposition) onto the jaw members 110 and 120. For example, one technique involves thermally spraying a ceramic material onto the surface of the jaw member 110 and 120 to form the stop members 750. Several suitable thermal spraying techniques may be utilized including, for example, depositing a broad range of heat resistant and insulative materials on various surfaces to create stop members 750 for controlling the gap distance between electrically conductive surfaces 112 and 122.

In embodiments, the present disclosure may incorporate a knife assembly (not shown) that, when activated via the trigger assembly 70, progressively and selectively divides tissue along an ideal tissue plane in a precise manner to effectively and reliably divide the tissue.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A bipolar forceps, comprising:
    an end effector assembly having a flexible jaw member and a fixed jaw member, the flexible jaw member having a flange extending therefrom operably coupled to the fixed jaw member about a pivot;
    a drive assembly operably coupled to the flange and configured to pivot the flexible jaw member relative to the fixed jaw member from a first position wherein the flexible jaw member is disposed in spaced relation relative to the fixed jaw member and a second position wherein the flexible jaw member is closer to the fixed jaw member;
    a handle operably coupled to the drive assembly and movable between an open position when the jaw members are disposed in the first position and a closed position to cause the drive assembly to rotate the flange about the pivot in a second direction to move the jaw members to the second position; and
    wherein a distal end of the flexible jaw member is configured to engage the fixed jaw member prior to a proximal portion thereof upon movement of the jaw members to the second position such that the proximal portion is configured to flex toward the fixed jaw member when the distal end of the flexible jaw member contacts the fixed jaw member to grasp tissue between the jaw members.

2. A bipolar forceps according to claim 1, wherein the handle is configured, when in the closed position, to generate additional torque about the pivot to impart a load on the drive assembly to vary a predetermined closure force between the jaw members.

3. A bipolar forceps according to claim 1, wherein the handle is configured to be squeezed when in the closed position to generate a closure force to the flexible jaw member to vary a predetermined closure force between the jaw members.

4. A bipolar forceps according to claim 2, wherein the predetermined closure force between the jaw members is in the range of about 3 kg/cm$^2$ to about 16 kg/cm$^2$.

5. A bipolar forceps according to claim 2, wherein the flange, upon movement thereof about the pivot in the second direction, engages a camming member to prevent further movement of the flange about the pivot in the second direction when the jaw members are in the second position, wherein subsequent squeezing of the handle is configured to flex the flexible jaw member to the vary the predetermined closure force between the jaw members when the jaw members are in the second position.

6. A bipolar forceps according to claim 1, wherein at least one of the jaw members includes a series of stop members disposed thereon configured to regulate the distance between the jaw members during tissue sealing.

7. A bipolar forceps according to claim 1, wherein the flexible jaw member is formed from one of aluminum, aluminum alloy, plated brass, stainless steel, stainless steel alloy, and beryllium copper.

8. A bipolar forceps according to claim 1, wherein the flange includes a mechanical interface operably coupled to the drive assembly, the drive assembly configured to urge the mechanical interface proximally to rotate the flange about the pivot to move the flexible jaw towards the stationary jaw and distally to rotate the flange about the pivot to move the flexible jaw into spaced relation relative to the stationary jaw member.

9. A bipolar forceps according to claim 1, further comprising:
    a rotating assembly for rotating the jaw members about the longitudinal axis defined through the shaft.

10. A bipolar forceps, comprising:
    a housing having a shaft that extends therefrom, the shaft defining a longitudinal axis therethrough and having an end effector assembly at a distal end thereof, the end effector assembly having a moveable flexible jaw member and an inflexible jaw member, the flexible jaw member having a flange extending therefrom operably coupled to the inflexible jaw member about a pivot, each of the flexible jaw member and the inflexible jaw member adapted to connect to a source of electrical energy such that electrical energy can be conducted through tissue to effect a seal;

a drive assembly operably coupled to the flange and configured to rotate the flange about the pivot to move the flexible jaw member relative to the inflexible jaw member from a first position wherein the flexible jaw member is disposed in spaced relation relative to the inflexible jaw member and a second position wherein the flexible jaw member is closer to the inflexible jaw member; and a handle operably coupled to the drive assembly and movable between an open position to cause distal movement of the drive assembly which rotates the flange in a first direction about the pivot to move the jaw members to the first position and a closed position to cause proximal movement of the drive assembly which rotates the flange in a second direction about the pivot to move the jaw members to the second position to maintain a predetermined closure force therebetween, wherein the handle is configured, when in the closed position, to cause at least a portion of the flexible jaw member to flex toward the inflexible jaw member and generate additional torque about the pivot to impart a load on the drive assembly to vary the predetermined closure force between the jaw members.

11. A bipolar forceps according to claim 10, wherein the jaw members are each movable relative to each other to grasp tissue therebetween.

12. A bipolar forceps according to claim 10, wherein the flange includes a mechanical interface operably coupled to the drive assembly, the drive assembly configured to urge the mechanical interface proximally to rotate the flange about the pivot to move the flexible jaw member towards the inflexible jaw member and distally to rotate the flange about the pivot to move the flexible jaw member into spaced relation relative to the inflexible jaw member.

13. A bipolar forceps according to claim 10, wherein the flange, upon movement thereof about the pivot in the second direction, engages a camming member to prevent further movement about the pivot in the second direction to regulate the predetermined closure force between the jaw members when the jaw members are in the second position.

14. A method of utilizing a bipolar forceps, the method comprising the steps of:

providing an end effector assembly having a flexible jaw member operably coupled to a fixed jaw member about a pivot; and pivoting the flexible jaw member relative to the fixed jaw member from a first position wherein the flexible jaw member is disposed in spaced relation relative to the fixed jaw member and a second position wherein a distal end of the flexible jaw member is configured to engage the fixed jaw member prior to a proximal portion thereof such that the proximal portion is configured to flex toward the fixed jaw member when the distal end of the flexible jaw member contacts the fixed jaw member to grasp tissue between the jaw members.

15. A method according to claim 14, further comprising the step of:

generating a closure force to the flexible jaw member when the jaw members are in the second position to vary a predetermined closure force therebetween.

16. A method according to claim 14, further comprising the step of:

providing a camming member configured to engage the flexible jaw member upon movement thereof to the second position to regulate a predetermined closure force between the jaw members when the jaw members are in the second position.

17. A method according to claim 14, further comprising the step of:

providing a series of stop members disposed on at least one of the jaw members to regulate the distance between the jaw members during tissue sealing.

* * * * *